United States Patent [19]
Joliot et al.

[11] Patent Number: 5,888,762
[45] Date of Patent: Mar. 30, 1999

[54] NEUROTROPIC GROWTH FACTORS COMPRISING A HOMEOBOX PEPTIDE

[75] Inventors: Alain Joliot; Alain Prochiantz, both of Paris, France

[73] Assignee: Centre National De La Recherche Scientifique (CNRS), Paris, France

[21] Appl. No.: 238,518

[22] Filed: May 5, 1994

Related U.S. Application Data

[63] Continuation-in-part of Ser. No. 828,995, Mar. 27, 1992, abandoned.
[51] Int. Cl.$^6$ .......................... C12P 21/06; C07K 14/475; C12N 5/00
[52] U.S. Cl. .................... 435/69.1; 435/69.7; 435/240.1; 514/2; 514/44; 530/300
[58] Field of Search .......................... 530/300; 435/69.1, 435/69.7, 240.1; 514/2, 44

[56] References Cited

PUBLICATIONS

*Daniele Derossi et al*, "The Third Helix of the Antennapedia Homeodomain Translocates Through Biological Membranes," The Journal of Biological Chemistry, vol. 269, No. 14, pp. 10444–10450 (Apr. 8, 1994).

*Isabelle le Roux et al*, "Neurotrophic Actiity of the Antennapedia Homeodomain Depends on its Specific DNA–Binding Properties," Proc. Natl. Acad. Sci. USA, vol. 90, pp. 9120–9124 (Oct. 1993).

*E. Bloch–Gallego et al*, "Antennapedia Homeobox Peptide Enhances Growth and Branching of Embryonic Chicken Motoneurons in Vitro," The Journal of Cell Biology, vol. 120, No. 2, pp. 485–492 (Jan. 1993).

*F. Perez et al*, "Antennapedia Homeobox as a Signal for the Cellular Internalization and Nuclear Addressing of a Small Exogenous Peptide," Journal of Cell Science, vol. 102, pp. 717–722 (1992).

Bodner et al 1988 Cell 55:505–518.
Nourse et al 1990 Cell 60: 535–545.
Joliot et al 1991 New Biologist 3(11) : 1121–1134.
Müller et al 1988 EMbO J 7(13); 4299–4304.
Le Maitre et al 1987 PNAS 84: 648–652.
Joliot et al 1991 PNAS 88: 1864–1868.

*Primary Examiner*—Vasu Jagannathan
*Assistant Examiner*—Karen Cochrane Carlson
*Attorney, Agent, or Firm*—Oblon, Spivak, McClelland, Maier & Neustadt, P.C.

[57] ABSTRACT

The invention relates to a method for introducing a macromolecule comprising at least the helix 3 of a homeobox peptide into a living cell. In particular the macromolecule is active as a cell growth factor, in particular a neurotrope.

20 Claims, 4 Drawing Sheets

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 60 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

```
Arg Lys Arg Gly Arg Gln Thr Tyr Thr Arg Tyr Gln Thr Leu Glu Leu
 1               5                   10                  15

Glu Lys Glu Phe His Phe Asn Arg Tyr Leu Thr Arg Arg Arg Arg Ile
                20                  25                  30

Glu Ile Ala His Ala Leu Cys Leu Thr Glu Arg Gln Ile Lys Ile Trp
            35                  40                  45

Phe Gln Asn Arg Arg Met Lys Trp Lys Lys Glu Asn
        50                  55                  60
```

( 2 ) INFORMATION FOR SEQ ID NO:2:

( i ) SEQUENCE CHARACTERISTICS:
        ( A ) LENGTH: 10 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:2:

A N N N N C A T T A                                                                                                                                   1 0

( 2 ) INFORMATION FOR SEQ ID NO:3:

( i ) SEQUENCE CHARACTERISTICS:
        ( A ) LENGTH: 27 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

Ile  Ala  His  Ala  Leu  Cys  Leu  Thr  Glu  Arg  Gln  Ile  Lys  Ile  Trp  Phe
    1                    5                              1 0                              1 5

Gln  Asn  Arg  Arg  Met  Lys  Trp  Lys  Lys  Glu  Asn
                        2 0                                    2 5

( 2 ) INFORMATION FOR SEQ ID NO:4:

( i ) SEQUENCE CHARACTERISTICS:
        ( A ) LENGTH: 30 base pairs
        ( B ) TYPE: nucleic acid
        ( C ) STRANDEDNESS: unknown
        ( D ) TOPOLOGY: linear ( i i ) MOLECULE TYPE: DNA (genomic)

( x i ) SEQUENCE DESCRIPTION: SEQ ID NO:4:

G G G G G A A T T C    C A T A T G C G C A    A A C G C G C A A G                                             3 0

( 2 ) INFORMATION FOR SEQ ID NO:5:

( i ) SEQUENCE CHARACTERISTICS:
        ( A ) LENGTH: 40 base pairs
        ( B ) TYPE: nucleic acid
        ( C ) STRANDEDNESS: unknown
        ( D ) TOPOLOGY: linear ( i i ) MOLECULE TYPE: DNA (genomic)

( x i ) SEQUENCE DESCRIPTION: SEQ ID NO:5:

G G G G A A G C T T    G G A T C C T C A G    T T C T C C T T C T    T C C A C T T C A T                  4 0

( 2 ) INFORMATION FOR SEQ ID NO:6:

( i ) SEQUENCE CHARACTERISTICS:
        ( A ) LENGTH: 26 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:6:

C A G A G C A C G T    G A T T A C C C C C    T C A A C C                                                       2 6

( 2 ) INFORMATION FOR SEQ ID NO:7:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

```
Thr Glu Arg Gln Ile Lys Ile Trp Phe Gln Asn Arg Arg Met Lys Trp
1               5                   10                  15
Lys Lys Glu Asn
            20
```

( 2 ) INFORMATION FOR SEQ ID NO:8:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:8:

```
Arg Gln Ile Lys Ile Trp Phe Gln Asn Arg Arg Met Lys Trp Lys Lys
1               5                   10                  15
```

( 2 ) INFORMATION FOR SEQ ID NO:9:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:9:

```
Arg Lys Arg Gly Arg Gln Thr Tyr Thr Arg Tyr Gln Thr Leu Glu
1               5                   10                  15
```

( 2 ) INFORMATION FOR SEQ ID NO:10:

( i ) SEQUENCE CHARACTERISTICS:
        ( A ) LENGTH: 60 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:10:

```
Arg Lys Arg Gly Arg Gln Thr Tyr Thr Arg Tyr Gln Thr Leu Glu Leu
1               5                   10                  15
Glu Lys Glu Phe His Phe Asn Arg Tyr Leu Thr Arg Arg Arg Arg Ile
            20              25                  30
Glu Ile Ala Tyr Ala Leu Cys Leu Thr Glu Arg Gln Ile Lys Ile Trp
            35              40                  45
Phe Ala Asn Arg Arg Met Lys Trp Lys Lys Glu Asn
            50              55              60
```

( 2 ) INFORMATION FOR SEQ ID NO:11:

( i ) SEQUENCE CHARACTERISTICS:
        ( A ) LENGTH: 58 amino acids
        ( B ) TYPE: amino acid
        ( D ) TOPOLOGY: linear ( i i ) MOLECULE TYPE: peptide (xi) SEQUENCE DESCRIPTION: SEQ ID NO:11:

```
Arg Lys Arg Gly Arg Gln Thr Tyr Thr Arg Tyr Gln Thr Leu Glu Leu
1               5                   10                  15
Glu Lys Glu Phe His Phe Asn Arg Tyr Leu Thr Arg Arg Arg Arg Ile
            20                  25                      30
Glu Ile Ala His Ala Leu Cys Leu Thr Glu Arg Gln Ile Lys Ile Ser
        35              40                      45
Asn Arg Arg Met Lys Trp Lys Lys Glu Asn
    50                  55
```

(2) INFORMATION FOR SEQ ID NO:12:

(i) SEQUENCE CHARACTERISTICS:
        (A) LENGTH: 60 amino acids
        (B) TYPE: amino acid
        (D) TOPOLOGY: linear (ii) MOLECULE TYPE: peptide (xi) SEQUENCE DESCRIPTION: SEQ ID NO:12:

```
Arg Lys Arg Gly Arg Gln Thr Tyr Thr Arg Tyr Gln Thr Leu Glu Leu
1               5                   10                  15
Glu Lys Glu Phe His Phe Asn Arg Tyr Leu Thr Arg Arg Arg Arg Ile
            20                  25                      30
Glu Ile Ala His Ala Leu Cys Pro Pro Glu Arg Gln Ile Lys Ile Trp
        35              40                      45
Phe Gln Asn Arg Arg Met Lys Trp Lys Lys Glu Asn
    50                  55                  60
```

NEUROTROPIC GROWTH FACTORS COMPRISING A HOMEOBOX PEPTIDE

CROSS REFERENCE TO RELATED APPLICATIONS

This application is a continuation-in-part of U.S. application Ser. No. 07/828,995, filed Mar. 27, 1992, now abandoned, which is a U.S. National Stage application of PCT/FR91/00444, filed Jun. 5, 1991.

BACKGROUND OF THE INVENTION

1. Field of the Invention

The present invention relates to the use of homeobox peptides or peptides derived therefrom for the production of medicinal products.

2. Discussion of the Background

The name homeobox peptides denotes a family of related peptide sequences which occur in various animal species in the products of genes involved in embryogenesis.

Indeed, genes are known which are expressed at various stages of embryo development and whose expression controls the cell migration and differentiation phenomena involved in the morphogenesis of the organism.

These genes are called homeotic genes and their translational products are called homeoproteins.

One of these genes, which has been most particularly studied, is the Antennapedia gene of Drosophila; the analysis of this gene has made it possible to identify a DNA sequence of about 180 bp, called homeobox sequence.

This homeobox sequence has the characteristic of being highly conserved in many homeotic genes, and this not only in Drosophila, but also during the course of evolution, in various animal species. Homeobox sequences homologous to that of Drosophila have thus been found in all vertebrates including mammals [ACAMPORA et al., NUCLEIC ACID RES., 17, 10385, (1989)].

The homeobox sequence encodes a polypeptide sequence of 60 amino acids which corresponds to a structurally and functionally conserved region which is present in all homeoproteins, the homeodomain. The sequence of the homeodomain which is encoded by the homeobox sequence of the Antennapedia gene (SEQ ID NO: 1)is indicated below by way of example.

NH2-Arg Lys Arg Gly Arg Gln Thr Tyr Thr Arg Tyr Gln Thr Leu Glu Leu Glu Lys Glu Phe His Phe Asn Arg Tyr Leu Thr Arg Arg Arg Arg Ile Glu Ile Ala His Ala Leu Cys Leu Thr Glu Arg Gln Ile Lys Ile Trp Phe Gln Asn Arg Arg Met Lys Trp Lys Lys Glu Asn-COOH.

The role and the mechanism of action of the homeodomain sequence have been the subject of various research studies. It is thus currently known that this sequence allows the binding of the homeoproteins to DNA in the region of consensus sequences containing the unit ATTA, which are present in the promoters or in the enhancer sequences of various genes, including the homeobox-containing genes themselves.

MULLER et al [EMBO J., 7, 4299, (1988)] have cloned the homeobox sequence of Antennapedia and purified the corresponding polypeptide or homeobox peptide (pAntp). In the presence of a reducing agent, they obtained the polypeptide in the form of a monomer with a sedimentation coefficient of about 1 S and with an apparent molecular weight of 9040 Da (theoretical molecular weight, based on the peptide sequence=8545 Da).

In the absence of a reducing agent, the polypeptide preparation contained a high proportion of dimers corresponding to homeodomains attached to each other via disulphide bridges.

These same authors also showed that the polypeptide purified in monomeric form became bound to the DNA in the region of a sequence ANNNNCATTA, (SEQ ID NO: 2) which therefore contains the consensus sequence ATTA.

Other research work [OTTING et al., EMBO J., 7, 4305, (1988)] has established that the homeodomain has a special structure (helix/β-turn/helix) which is reported to be involved in the binding to DNA.

The homeobox peptide/DNA binding is reported to be the resultant:

of a high-affinity binding ($K_D 10^{-9}$–$10^{-10}$M), involving the consensus sequence ATTA, and of a low-affinity binding ($K_D 10^{-6}$–$10^{-7}$M), involving the wide groove of the DNA double helix.

A publication by KISSINGER et al. [Cell, 63, 579–590, (1990)] describes a crystallographic study on an "engrailed homeodomain/DNA" complex. This study shows that the C-terminal portion of the homeodomain, comprising in particular the structure called helix 3 (amino acids 42–58 of the engrailed homeodomain), binds to the wide groove of the DNA. This binding is essentially brought about by hydrophilic interactions; this binding is reported to be independent of the presence of the consensus sequence.

All known homeodomains share the same helix/β-turn/helix structure, despite some differences in their primary sequences.

Given the very high degree of conservation of the homeobox sequences from one species to another, it is considered that the properties of the homeobox peptide pAntp can be extended to other homeobox peptides which may differ in their sequence by a few amino acids but possess virtually identical functional properties. In the following text, the term "homeobox peptide" will designate any peptide having the full-length sequence of an homeodomain as defined above, and able to fold into the helix/β-turn/helix structure. This includes, for instance, the peptide pAntp or any other member of the same family or of a related family, for example the "engrailed" family.

"Helix 3" is understood to mean the portion of an homeobox peptide as defined above, which is involved in the low-affinity binding with the wide groove of the DNA. According to the definition provided by BURGLIN [Cell, 53, 339–340, (1988)] helix 3 extends from amino-acid 43 to amino-acid 58 of the homeobox peptide. Within the context of the present invention "helix 3" also refers to peptides which may slightly differ in their sequence from the helix 3 of naturally occurring homeodomains, provided that said differences have no influence on the structure of said helix 3 and to its ability to bind to the DNA double helix.

Such polypeptides may for instance result from the substitution of an amino-acid by another, according to the known "groups of substitution" of aminoacids, since it is known in the art that conservative substitution of one hydrophobic, aromatic, aliphatic, acidic or basic residue for another in a peptide frequently does not alter the structural characteristics of said peptide.

Although numerous data, obtained in vitro and in an acellular system, are now available on the homeobox peptide/DNA binding, the effects on cellular functions were unknown up until now. It was not even known whether the homeobox peptides were capable of having an inherent activity or whether their role was simply limited to allowing the homeoprotein/DNA binding.

However, by studying the action of synthetic homeobox peptides on cell cultures, the Inventors have discovered unexpected properties of the said peptides, properties which had never been thought of up until then.

Indeed, they observed that the synthetic homeobox peptides, when they are added to cultured nerve cells, penetrate into all the cells of the culture and that the entry of the peptides into the neurons is followed by accumulation in the nucleus. This accumulation is blocked not only by preincubation with an oligonucleotide containing the consensus sequence ATTA, but also by preincubation with fragments of double-stranded DNA not containing the consensus sequence.

By analysing this penetration process, the Inventors demonstrated the importance therein of the region corresponding to the helix 3+4 (last 27 amino acids of the homeobox peptide).

They also observed the penetration of polypeptides comprising this homeobox peptide.

They also observed this phenomenon, although to a lesser degree, in cultures of cells other than nerve cells.

The Inventors also showed that the accumulation of homeobox peptides in the nucleus was accompanied by intense cell growth and differentiation.

These properties of the homeobox peptides, which have been demonstrated by the Inventors, allow their use for the production of new medicinal products as well as their use in vitro as an agent which is active on cell cultures.

Indeed, it stems from the research work by the Inventors that the homeobox peptides or fragments thereof, are capable of providing new, in particular neurotropic, growth factors and/or new vectors for the transmembrane and intracellular transport of molecules, in particular peptides and oligonucleotides, which are active on the cellular functions.

However, both of these applications correspond to current needs. They have been the subject of various research work of which a brief overview is given below.

The importance of the intracellular vectors for the transport of peptides or oligonucleotides became apparent following the demonstration that some peptides and oligonucleotides, by binding specifically to certain DNA regions, were capable of acting on the cellular functions (for example, proteins activating or repressing the expression of a gene, antisense oligonucleotides and the like).

However, an effective exploitation, in particular for a therapeutic objective, of the properties of these molecules involves delivering them to the site by causing them to cross numerous barriers, in particular the cytoplasmic membrane, separating the extracellular medium from the DNA. However, very often, these molecules, by virtue of their charge and their high molecular mass, are unable to cross this barrier by themselves. Various solutions have been proposed to this problem; some of them, relating to oligonucleotide sequences, are for example mentioned in the introduction in the publication by LEMAITRE et al. [Proc. Natl. Acad. Sci. USA 84, 648–652 (1987)]. For their part, these authors propose an approach consisting of covalently binding an oligonucleotide sequence which is complementary to an RNA sequence of the vesicular stomatitis virus (VSV), to (L-lysine) polymer.

The conjugate obtained penetrates into the cells and inhibits specifically the synthesis of the VSV proteins in the infected cells.

These results show the importance of the association between an active macromolecule and a vector for the transport of the said macromolecule. It is therefore particularly desirable to search for new vectors.

In the case of the growth factors which are active on the survival and the differentiation of the neurons, only a small number are currently known; the first one to be identified is the Nerve Growth Factor (NGF). The action of the NGF is exerted essentially on the sensory neurons and the neurons of the sympathetic nervous system; an action on certain cells of the central nervous system and of the immune system has also been detected. The neurotropic activity of the NGF is carried by a subunit ($\beta$ subunit) of 118 amino acids.

Other substances with neurotropic action have also been described: they are for example, the Ciliary Neurotropic Factor (CNTF) [LIN et al, SCIENCE, 246, 1023–1026, (1989); STOCKLI et al. NATURE, 342, 920–923, (1989)], the Brain Derived Neurotropic Factor (BDNF) [LEIBROCK et al., NATURE, 341, 149–152, (1989)], the Glial Derived Nexin (GDN), a component of the extracellular matrix [GLOOR et al., CELL, 47, 687–693, (1986)],.

More ubiquitous growth factors such as Fibroblast Growth Factor (FGF) [PARK and HOLLENBERG, DEV. BIOL., 134, 201–205, (1989)] or the Epidermal Growth Factor (EGF) [MORRISON et al., SCIENCE, 238, 72–74, (1987)] also have a neurotropic action.

The mechanism of action of these factors is currently not well known. It has been shown that the NGF penetrates into the neurons via a specific receptor which is a phosphorylated glycoprotein [CHAO et al., Science, 232, 518 (1986)]. Inside the nerve cell, the NGF stimulates the synthesis of RNA via a second messenger.

Many experiments show the potential therapeutic importance of neurotropic growth factors.

The use of NGF has for example been suggested in Alzheimer's disease. It has indeed been shown that NGF makes it possible to increase the choline acetyltransferase activity of the cholinergic neurons and to prevent their degeneration [MOBLEY et al, Science, 229, 284 (1984)], [KROMER, Science, 235, 214, (1987)]. However, it is known that Alzheimer's disease is associated with degeneration of the cholinergic neurons and with a decrease in the choline acetyltransferase activity.

Experiments carried out in adult rats in which the cholinergic route linking the hippocampus and the septum had previously been destroyed (which results in degeneration of the septal neurons) have shown that the intraventricular injection of NGF allows the survival of the septal neurons as well as the restoration of a normal choline acetyltransferase activity [WILL et HEFTI, Behav. Brain. Res., 17,17 (1985)]. The use of neurotropic growth factors has also been envisaged in the case of Parkinson's disease which is linked to a degeneration of the dopaminergic neurons.

Another approach to the treatment of diseases associated with a neuronal degeneration has recently been proposed and appears set, in a new future, for a major development; it is the intracerebral transplantations of cells which are capable of making up for the defective neuronal functions; the use of fetal neurons [LINDVALL et al., SCIENCE, 247, 574–577, (1990)] or of transformed cell lines [HORELLOU et al., EUR. J. NEUROSCI., 2, 116–119, (1990)] has thus been suggested.

Recently, transformed cells, producing a recombinant NGF, were implanted in the brain of rats at the same time as cholinergic neurons of fetal origin. It was observed that, under these conditions, the survival of the transplanted neurons as well as the neogenesis of the nerve fibres was greatly increased [ERNFORS et al., Proc. Natl. Acad. Sci. USA, 86, 4756, (1989)].

These research studies therefore show that neurotropic growth factors can find particularly advantageous applications in the treatment of disorders resulting from neuronal lesions or degeneration.

A limitation in the use of neurotropic growth factors, however, consists of the small number of growth factors currently known, as well as of their relatively narrow specificity of action which is limited to certain types of neurons. Furthermore, most of these growth factors currently cannot be obtained in sufficient amount for a therapeutic use.

It would therefore be particularly desirable to have neurotropic growth factors which do not possess the disadvantages that have just been mentioned.

SUMMARY OF THE INVENTION

The Invention results from the discovery of the unexpected properties of the homeobox peptide to enter the intact living cells, said property depending of the presence of the helix 3, and further to enhance the neuronal growth.

The present invention, by the demonstration of these unexpected properties, proposes a new response to both of the problems which have just been set out above.

The properties of transmembrane penetration and intracellular transport of the homeobox peptides and their fragments comprising helix 3 allow their use as a carrier for introducing into the living cells molecules of interest which are active on the cellular functions, in particular other peptides, or nucleotide sequences.

An object of the invention is to provide a method for introducing a macromolecule into a living cell, which method comprises contacting said living cell with said macromolecule, which comprises at least the helix 3 of an homeobox peptide.

BRIEF DESCRIPTION OF THE DRAWINGS

FIG. 1A shows the appearance of control cells cultured for 24 hours in the absence of peptide. FIG. 1B shows the appearance of the cells cultured for 24 hours in the presence FIG. 2A demonstrates that the homeobox peptide is rapidly captured by all the neurons and then transported into the nucleus. FIG. 2B demonstrates that this transport is blocked after preincubation with the consensus oligonucleotide obtained from the Hox1.3 promoter or alternatively with a mixture of fragments of random sequence double helix DNA.

FIG. 3A shows that the labeled pAntp is mainly found in the nucleoplasm. FIG. 3B demonstrates that polyornithine is present in the soma and the nucleoli.

FIG. 4A demonstrates that basal protein kinase C (PKC) phosphorylation is not antagonized after a two hour incubation with the PKC-inhibiting peptide alone. FIG. 4B demonstrates that a 2 hour incubation with the inhibitor peptide linked to the helix 3 peptide completely inhibits phosphorylation of the PKC sites but does not modify phosphorylation of the non-PKC sites. FIG. 4C demonstrates that incubation of the cells with PKC-inhibiting peptide alone does not abolish the increased phosphorylation upon addition of phorbol ester. FIG. 4D demonstrates phorbol ester-induced increase of phosphorylation being abolished by a 2 hour preincubation with the PKC inhibitor linked to the helix 3 peptide.

DESCRIPTION OF THE PREFERRED EMBODIMENTS

Figure 1A:
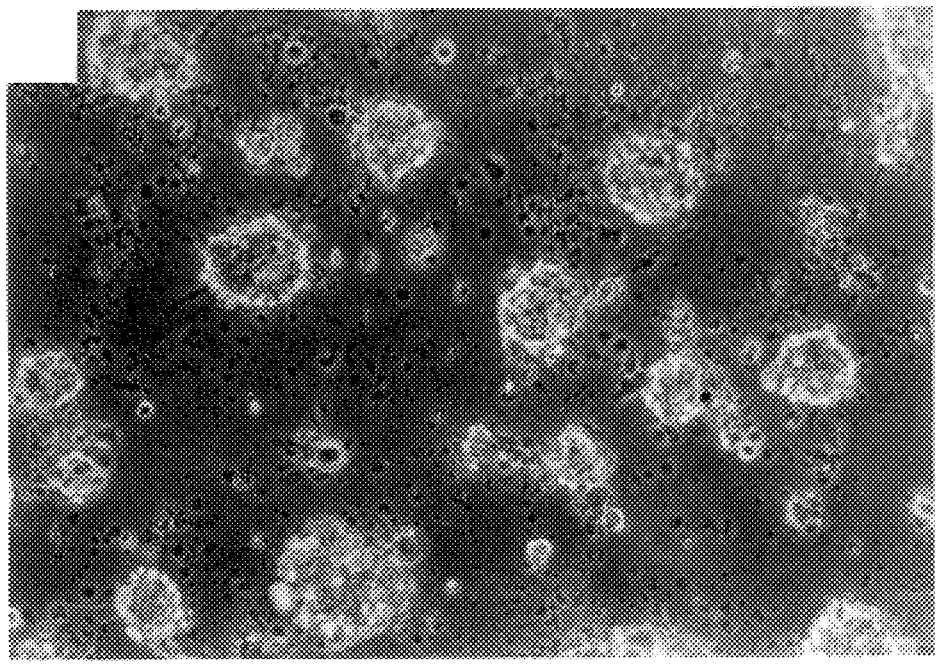
FIG. 1A and 1B depict the effects on cells of incubation with the pAntp peptide.

According to a preferred embodiment of the present invention, the homeobox peptide is the pAntp peptide.

Preferably, said macromolecule is selected from the group consisting of:

peptides comprising at least helix 3 of an homeobox peptide, and products of fusion of said peptides with an heterologous peptidic sequence, or with an oligonucleotide.

More preferably said macromolecule is selected from the group consisting of: an homeobox peptide, fragments thereof comprising at least helix 3, and their products of fusion with an heterologous peptidic sequence, or with an oligonucleotide.

"Product of fusion" refers herein to a macromolecule wherein a peptide comprising at least helix 3 is linked to another peptidic sequence or to a nucleotidic sequence, by a covalent bond.

The homeobox peptides, or fragments thereof, as well as their products of 3 fusion with another polypeptide sequence can be easily obtained by processes which are known per se, for example by peptide synthesis or alternatively by genetic engineering. Known techniques to obtain the products of fusion of a homeobox peptide and an oligonucleotide sequence include for example the technique described by LEMAITRE et al.[Proc. Natl. Acad. Sci. USA, 84, 648–652 (1987)].

Other known methods which allow to obtain products of fusion of two peptides or of a peptide with an oligonucleotide, include for instance linkage through a disulfide bridge.

"Heterologous peptidic sequence" is considered herein to mean a peptidic sequence chosen in such a way that the product of fusion of said sequence with the homeobox peptide or its fragment has a sequence different from the sequence of a naturally occurring homeoprotein or homeodomain.

Furthermore, the affinity of homeobox peptide and helix 3 thereof for DNA may be used to facilitate the nuclear addressing of active molecules whose pharmacological properties depend from their interaction with DNA In the case wherein one wishes to transport in the cell a molecule which is active on the cellular functions through the recognition of a specific sequence of DNA or RNA, a peptide containing helix 3 which recognises, independently of the sequence, the structure of the DNA molecule (wide groove), can advantageously be used as a carrier; the binding to a specific DNA or RNA sequence is then brought about by the peptide or the oligonucleotide bound to said carrier peptide, without interference due to the recognition and binding of the consensus ATTA sequence.

According to a preferred embodiment of the Invention, the macromolecule transported into the cell is an homeobox peptide, which is active as a growth factor, in particular neurotropic growth factor, both in vivo and in vitro.

Unlike the neurotropic growth factors known in the prior art, the homeobox peptides are active on a large number of neuron types. The inventors observed in particular the activity of pAntp on nerve cells prepared from various regions of the embryonic central nervous system, in particular the spinal cord, the rhombencephalon, the ventral mesencephalon, the tectum and the cortex. The activity on the cortical cells is particularly surprising since so far, no expression of homeoproteins has been detected in this region of the brain.

The broad spectrum of action of the homeobox peptides makes them pharmacological agents of great importance, particularly in the treatment of neuronal lesions or degenerations. They can also be used in the field of intracerebral transplantations of neurons which are set to increase and for which it is essential to ensure the survival as well as the most rapid and most extensive increase in the volume of the cellular graft.

This can be carried out, for example, by preincubating the neurons to be grafted with the homeobox peptide, or alternatively by carrying out a simultaneous transplantation of the embryonic cells with transformant cells capable of synthesising and secreting the homeobox peptides or fusion peptides containing a homeobox sequence.

The subject of the present invention is also a process for the in vitro treatment of neurons intended for transplantation, which process is characterised in that the said neurons are incubated in the presence of at least one homeobox peptide.

The subject of the present invention is furthermore a cellular composition which can be used in neuron transplantation techniques, which composition is characterised in that it contains a combination of neurons which it is desired to transplant and transformant cells capable of synthesising and secreting a homeobox peptide.

A further object of the Invention is to provide new macromolecules for use in the method of the Invention. Said macromolecules are selected in the group consisting of:

a) a fragment of an homeobox peptide encompassing the helix 3;
b) a fragment as defined in a), bound to an heterologous peptidic sequence;
c) a fragment as defined in a) bound to an oligonucleotide;
d) an homeobox peptide bound to an heterologous peptidic sequence;
e) an homeobox peptide bound to an oligonucleotide.

The inventors also studied the action of the homeobox peptides not only in cell cultures but also on pluricellular organisms. They also observed that by virtue of the speed of penetration of the homeobox peptides, the latter entered in a localised manner into the cells adjacent to the point of injection.

This property offers the advantage, within the framework of a use on a living organism, of making it possible to apply, if it is desired, a very precise, localised treatment to a group of cells.

The present invention will be more clearly understood with the aid of the additional description below which refers to examples demonstrating the activity of the homeobox peptides and fragments thereof.

It goes without saying however that these examples are given solely as illustration of the subject of the invention and do not constitute in any manner a limitation thereof.

I) PRODUCTION OF A pANTP PEPTIDE.

EXAMPLE I

The sequence encoding the homeodomain of the Antennapedia gene of Drosophila was synthesised using the PCR technique, from the plasmid p903G which contains, between the BamHI and PvuII sites, a 600-bp fragment of Antp cDNA (GARBER et al., 1983). Both primers, whose sequence is indicated below, are used. The first primer: (SEQ ID NO: 4)

(5'GGGGGAATTCCATATGCGCAAACGCGCAAG 3')
contains an NdeI restriction site upstream of the initiation codon, and the a second primer: (SEQ ID NO: 5)

(5'GGGGAAGCTTGGATCCTCAGTTCTCCTTCT TCCACTTCAT 3')
contains a termination codon followed by a BamHI site. A plasmid called pAH1 was prepared by ligation of the 220-bp NdeI-BamHI fragment obtained by PCR, into the plasmid pET3a (ROSENBERG et al., 1987). The polypeptide was then expressed in E.coli BL 21 (Lys S). The transformant cells were cultured at 37° C. in LB medium in the presence of ampicillin and chloramphenicol (100 g each) up to an optical density $OD_{600}$=1.2. After incubating for 5 hours in the presence of 1 mM of IPTG, the cells were recovered by centrifugation (16,000 g, 15 min), washed three times with 50 mM phosphate buffer, pH 7.5, 400 mM NaCl, 2 mM EDTA, 1 mM PMSF, 1 mM DTT (buffer A) and then sonicated.

After centrifugation (16,000 g, 15 min) the supernatant was precipitated with streptomycin sulphate (20 mg/ml), with gentle stirring for 15 minutes at room temperature, and then centrifuged (16,000 g, 15 min). The supernatant was loaded directly onto an S-SEPHAROSE Fast Flow column (PHARMACIA), previously equilibrated with buffer A. The column was then washed with a large quantity of 50 mM phosphate buffer, pH 7.5, 0.5M NaCl and the pAntp peptide was eluted by applying an NaCl gradient (0.5 to 1M). The eluted peptide (3 mg/l of culture) was then dialysed for 24 hours against 50 mM phosphate buffer, pH 7.5, 150 mM NaCl.

The sequences of the amplified DNA segment and of the peptide were determined (APPLIED BIOSYSTEM 477) and it was checked that they corresponded to those of the Antennapedia homeobox. Analysis of the peptide by gel electrophoresis in the presence of SDS demonstrated the presence of a single band of molecular weight corresponding to that of the Antennapedia homeopeptide.

The sequence of the peptide obtained (SEQ ID NO: 1) is as follows:

NH2-Arg Lys Arg Gly Arg Gln Thr Tyr Thr Arg Tyr Gln ThrLeu Glu Leu Glu Lys Glu Phe His Phe Asn Arg Tyr Leu Thr Arg Arg Arg Arg Ile Glu Ile Ala His Ala Leu Cys Leu Thr Glu Arg Gln Ile Lys ILe Trp Phe Gln Asn Arg Arg Met Lys Trp Lys Lys Glu Asn-COOH

It was also checked by gel retardation of the peptide preincubated with an oligonucleotide duplex (SEQ ID NO: 6) corresponding to the binding site of a homeobox protein of the Antennapedia type, and obtained from the Hox1.3 promoter [Hox1.3p, (ODENWALD et al., GENES AND DEV., 3, 158, 1989)]:

3'CAGAGCACGTGATTACCCCCTCAACC 5'
5'GTCTCGTGCACTAATGGGGGAGTTGG 3'
that the peptide recognises in vitro the consensus sequence for the binding of the proteins of the Antennapedia type.

II) DEMONSTRATION OF THE PENETRATION OF pAntp INTO LIVING CELLS AND OF ITS ACTIVITY AS GROWTH FACTOR.

EXAMPLE II

Demonstration of the Biological Effect of the pAntp Peptide on Cultured Neurons

The neurons removed from rat embryos (E14 to E 16) in various regions of the brain (mesencephalon, spinal cord, cortex), are inoculated into a defined medium (CHAMAK and PROCHIANTZ, DEVELOPMENT, 106, 483, 1989) which permits the survival of only the neuronal cells (CDM medium).

The pAntp peptide is renatured by a 10-min incubation at 60° C. in the presence of dithiothreitol (0.1 mM) and magnesium (10 mM) in an isotonic phosphate buffer, pH 7.2 containing 33 mM D-glucose. The peptide is added to the nerve cells at a concentration of 9 g/ml (equivalent to 1.3M).

Figure 1B:
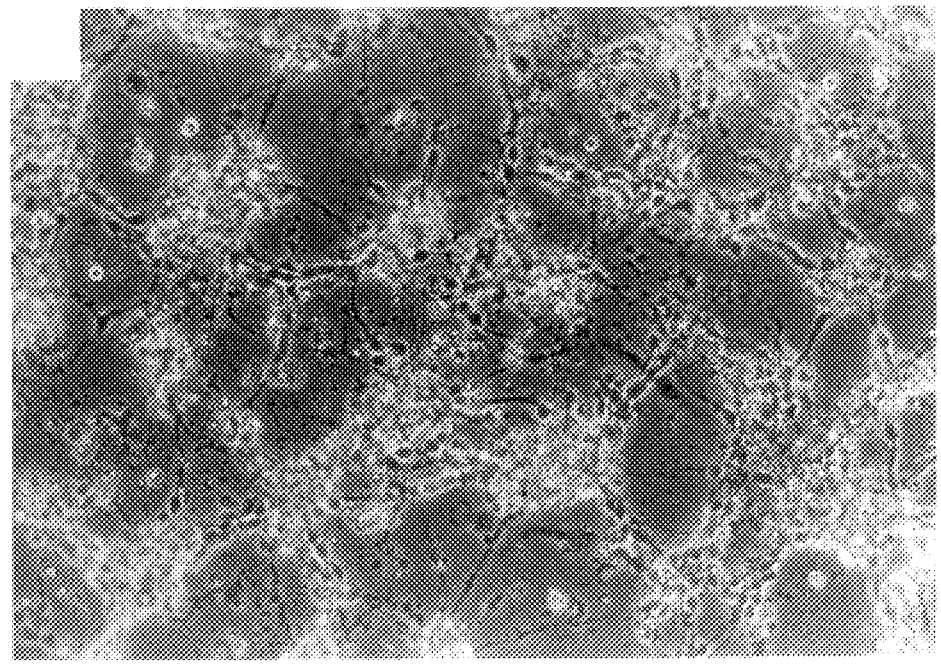

The effects observed after addition of the peptide are illustrated in FIG. 1 (A and B). FIG. 1A shows the appearance of control cells cultured for 24 hours in the absence of the peptide. FIG. 1B shows the appearance of the cells cultured for 24 hours in the presence of the peptide. A substantial increase in the neuritic growth is observed in the cells cultured in the presence of the pAntp peptide, starting from 24 h after the addition.

The same results for the cell growth were also observed during experiments in which the cells were preincubated with the pAntp peptide and then recultured for 24 hours in the CDM medium lacking the peptide. A 30 minute incubation in the presence of pAntp makes it possible even then to observe the effects described above; these effects are maximum after a 2-hour incubation and are not increased by prolonging the preincubation time.

Preincubation of the homeobox peptide with the consensus binding sequence obtained from the Hox1.3 promoter, or alternatively with a mixture of fragments (of random sequence) of double helix DNA, blocks its biological effect.

Figure 2A:
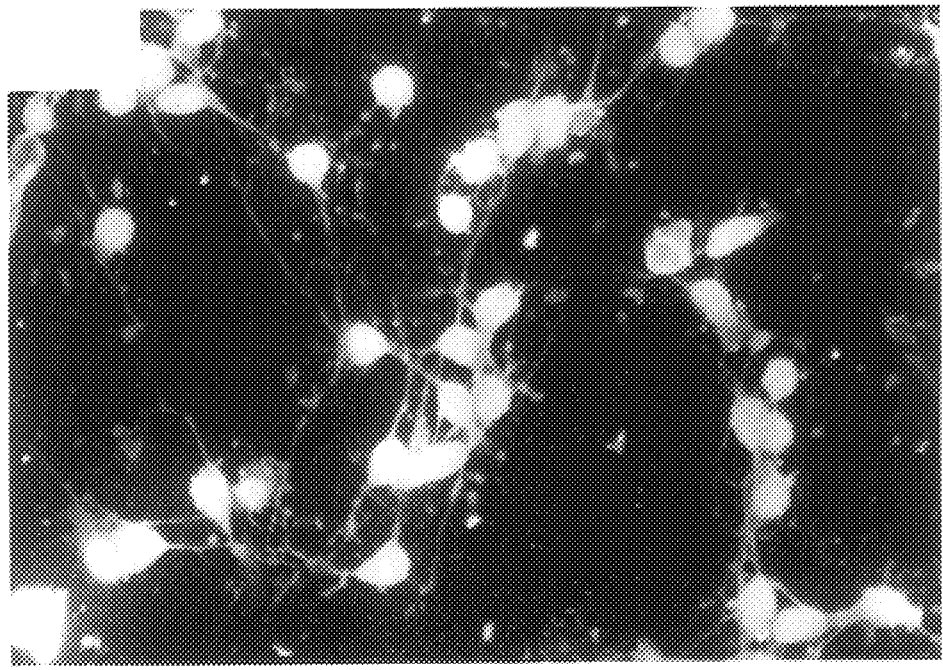
FIG. 2A and 2B are fluorescence micrographs demonstrating transport of a fluorescein-labeled peptide.
Figure 2B:

It was also shown, using a fluorescein-labelled peptide, that the homeobox peptide is rapidly (less than 2 hours) captured by all the neurons, and then transported into the nucleus (FIG. 2A), and that this transport is blocked after preincubation with the consensus oligonucleotide obtained from the Hox1.3 promoter or alternatively with a mixture of fragments (of random sequence) of double helix DNA (FIG. 2B).

A comparison between the entry and the intracellular distribution of the pAntp peptide and polyornithine was also made.

The cells were incubated for 1 hour in the presence of fluorescein-labelled pAntp or polyornithine.

Figure 3A:
FIG. 3A and 3B are fluorescence micrographs comparing the location of labeled pAntp to polyornithine.
Figure 3B:
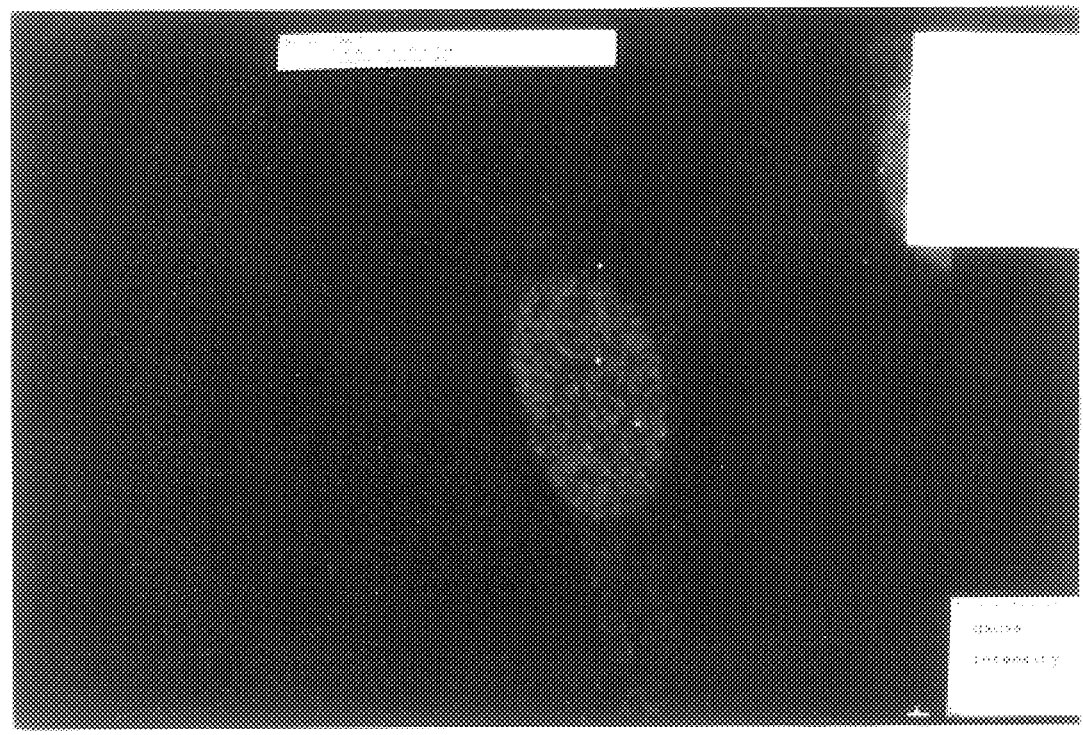
Figure 4A:
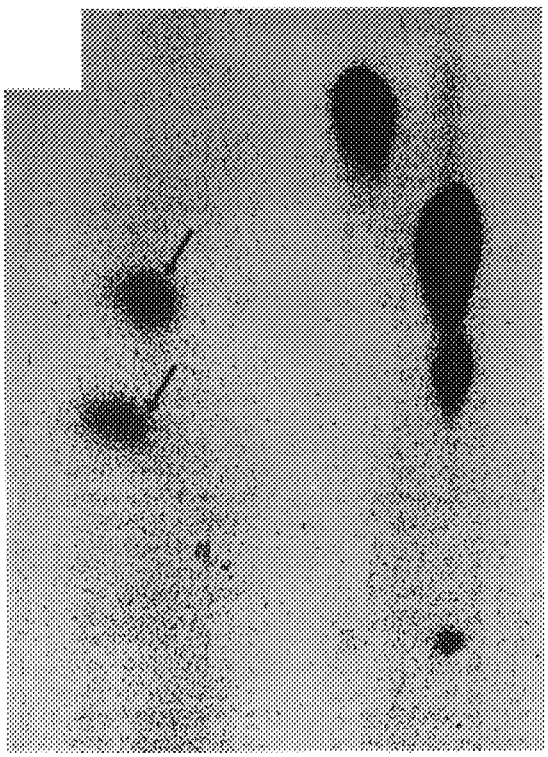
FIG. 4A–4D are peptide map which demonstrates the inhibition of intracellular protein kinase.
Figure 4B:
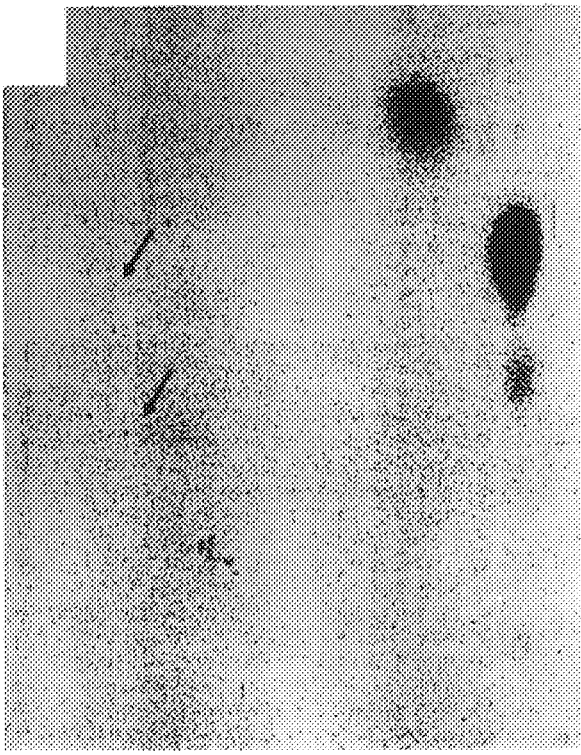
Figure 4C:
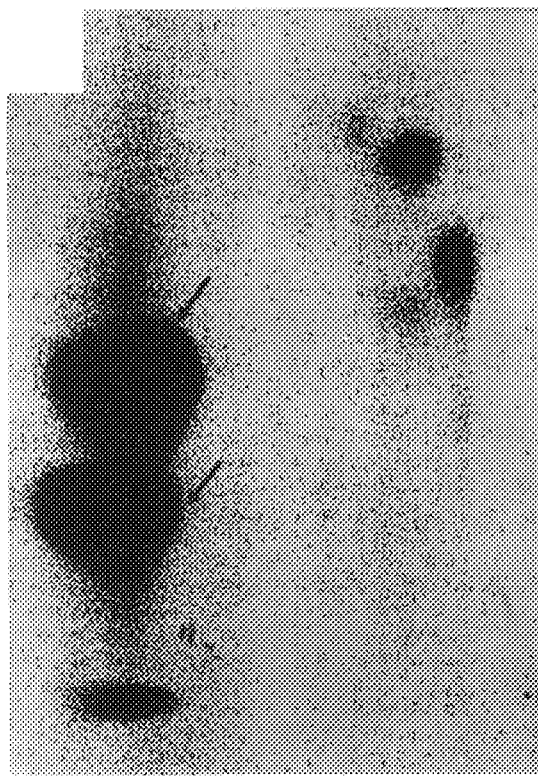
Figure 4D:
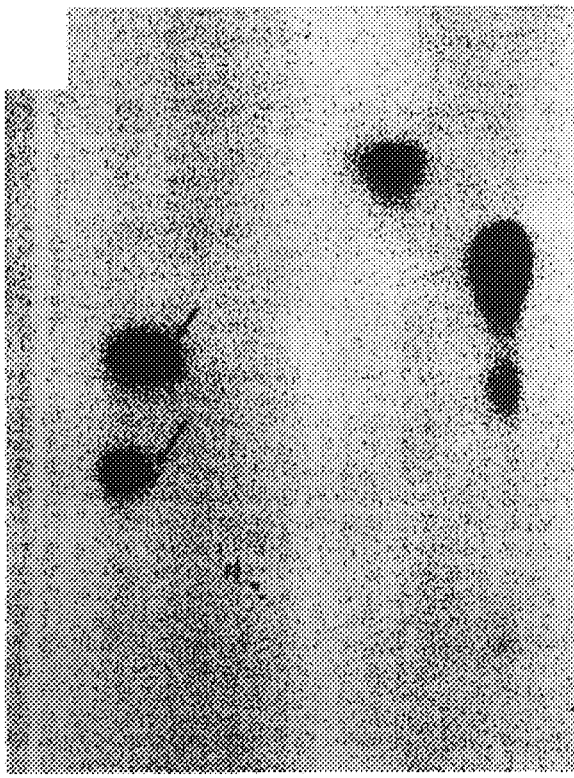

The results are illustrated by FIG. 3 which shows that the labelled pAntp (3A) is mainly found in the nucleoplasm, unlike the polyornithine which is present in the soma and the nucleoli (3B).

III) DEMONSTRATION OF THE ACTIVITY OF pAntp AND FRAGMENTS THEREOF AS INTERNALIZATION VECTORS

EXAMPLE III

Penetration of the pAntp Peptide Into Cultured Fibroblasts

The fibroblasts are obtained from the skin of rat embryos, mechanically dissociated and trypsinised; the cells are cultured in glass plates covered with poly-DL-ornithine (SIGMA, MW 40,000, 15 μg/ml), in DMEM-F12 culture medium (GIPCO-PRL) and in the presence of 10% fetal calf serum. After culturing for 24 hours, the cells are incubated for one hour in the presence of fluorescein-labelled pAntp peptide. The labelled pAntp peptide penetrates into the fibroblasts, but is present in the nucleus in a smaller quantity than in the nerve cells.

EXAMPLE IV

Penetration of the pAntp Peptide into Embryonic Cells in Vivo 0.2 μl of solution (1 μg/μl) of the fluorescein-labelled pAntp peptide are injected into the mesencephalon of 2-day old quail embryo. After incubating for 4 hours in ovo, the embryo is extracted from the egg and mesencephalon sections are prepared. Examination of these sections under the microscope shows that the fluorescent labelling is localised in the nucleus of the cells situated in the immediate vicinity of the point of injection.

EXAMPLE V

Penetration of Fragments of the pAntp Peptide Encompassing Helix 3

To further demonstrate the activity of helix 3 in cell internalization of the pAntp peptide, synthetic biotinylated peptides were prepared from the sequence of helix 3.

These peptides correspond respectively to amino-acids 41–60, (SEQ ID NO: 7) 43–58, (SEQ ID NO: 8) and 41–55 (SEQ ID NO: 9) of pAntp.

These peptides (10 μg/ml) were separately incubated with living neurons, at 37° C. for 3 hours.

After washing and fixation of the cells, the localisation of the peptides is checked by use of fluorinated streptavidin. Observation under microscope shows intracellular localization of the fluorescent label in the case of pAntp 41–60 and pAntp 43–58, but not in the case of pAntp 41–55.

Peptides having intermediate sequences between pAntp 43–58 and pAntp 41–55 were also tested. The results were identical with those observed with pAntp 41–55.

These results show that the shortest peptide able to penetrate the cell is pAntp 43–58, and that further deletions in helix 3 result in the loss of the ability to enter the cells. These results further demonstrate that helix 3 is the essential structure for the penetration of the homeobox peptide.

This experiment is disclosed with further details in a publication of DEROSSI et al. [J. Biol. Chem. 269, pp. 10444–10450 (1994)], the disclosure of which is incorporated herein by reference.

EXAMPLE VI

Penetration of Mutant pAntp Peptides

The influence of mutations in the homeobox sequence, inside and outside the helix 3 region, was tested.

Important mutations affecting the structure of the helix 3 are likely to impair the ability of homeobox peptide to enter the living cells; such mutations are for instance, deletions in helix 3, or substitutions of aminoacids believed to play an important role in the structure of helix 3.

Mutations outside helix 3, or mutations of lesser importance inside helix 3, such as substitution of amino-acids expected to have no influence in the structure of helix 3, are unlikely to affect the ability of the homeobox peptide to enter the living cells.

Having these considerations in mind, three mutant recombinant peptides were designed.

The first one (pAntp50A) has a substitution in position 50 of the homeodomain within the third helix. Position 50 was chosen because of its recognized importance in the sequence-specific interactions between homeodomains of different classes and specific consensus sequences of DNA. A mutation at this position is expected to impair the growth factor activity. However, since this position may be substituted without influence on the structure of helix 3, the corresponding mutant is expected to enter the cells.

The $Glu^{50} \rightarrow Ala^{50}$ modification was selected on the basis of the absence of $Ala^{50}$ in any of the classical homeodomain sequences available today, and also because the same modification results in the complete loss of recognition of both Bicoid and Antennapedia target sites by the homeobox peptide.

During the construction, of the recombinant peptide, a cloning artifact also introduced a His$^{36}$→Tyr substitution (SEQ ID NO: 10).

A second mutant (pAntp48S) corresponds to the replacement of three amino acids (Trp$^{48}$, Phe$^{49}$ and Glu$^{50}$) in helix 3 by a single serine residue (SEQ ID NO. 11). Trp$^{48}$ and Phe$^{49}$ are conserved in all homeodomains known so far, and hence are likely to be important for structural properties. Thus, the corresponding mutant is not expected to enter the cells.

A third mutant (pAntp40P2) corresponds to the substitution of Leu$^{40}$ and Thr$^{41}$, two amino-acids located in the turn between helix 2 and 3, by two proline residues (SEQ ID NO: 12). This modification which was mimicked by computational imaging impairs the correct folding of the helix-turn-helix motif, and is presumed to also impair neurite growth; however, since this structural modification takes place outside helix 3, the corresponding mutants are expected to enter the cells.

Peptides pAntp50A, pAntp48S, and pAntp40P2, labelled in E. coli with $^{35}$S-methionine were purified and added to dissociated rat embryonic neurons. After incubation for 2 hours, the medium was recovered by centrifugation and, after lysis of the cells with NP40, nuclear and post-nuclear fractions were isolated.

Identity of the radioactive material present in the nuclei was analysed by gel electrophoresis. Autoradiography confirmed that the radioactive species internalized corresponded to the original peptides with no obvious degradation.

After lysis of the neurons, peptide distribution in the different cell compartments and in the medium was quantified by determination of radioactivity in each fraction. The results presented in Table I below are the mean values (±standard deviation) of 6 different experiments. These results show that pAntp, pAntp50A and pAntp40P2 are internalized rapidly and that between 10 to 20% of the peptides reach the nuclei within 2 hours. As expected, pAntp48S was the only peptide unable to translocate through the membrane.

TABLE I

|  | NUCLEAR | POST-NUCLEAR | MEDIUM |
| --- | --- | --- | --- |
| pAntp | 17.0 ± 6 | 4.0 ± 1 | 79.0 ± 6.5 |
| pAntp40P2 | 11.5 ± 2 | 1.0 ± 0.5 | 87.5 ± 2.5 |
| pAntp50A | 19.0 ± 5 | 6.0 ± 1 | 75.0 ± 6 |
| pAntp48S | 2.5 ± 0.5 | 1.0 ± 0.5 | 96.5 ± 1 |

To confirm their internalization and nuclear accumulation, the peptides were fluoresceinated and incubated with the dissociated embryonic cells for 2 hours, as above. The cells were then washed, plated and cultured for 1 day before fixation. Observations by confocal microscopy show that pAntp, pAntp50A and pAntp40P2 mutants were taken up by all cells in the population and significant concentrations of the peptides accumulated in the nuclei.

As expected, none of the mutants pAntp40P2, pAntp50A, and pAntp48S was able to promote neurite growth.

This experiment is disclosed with further details in publications of LE ROUX et al. [Proc. Natl. Acad. Sci. USA, 90, 9120–9124 (1993)] and BLOCH-GALLEGO et al. [J. Cell. Biol. 120, 485–492 (1993)], the disclosure of which is incorporated herein by reference.

EXAMPLE VI

Internalization of Peptides Linked to pANTP

In order to demonstrate that chimeric peptides encompassing pAntp penetrate into cells, a chimeric peptide called AR3C was prepared. This chimeric peptide encompasses pAntp and the C-terminal region of rab3A, a small GTP-binding protein [ZAHRAOUI et al,. J. Biol. Chem., 12, 394–401 (1989)]. This chimeric construct, which has a molecular weight of 12 kDA, enters the cells and accumulates in the nuclei.

This experiment is disclosed with further details in a publication of PEREZ et al. [J. Cell. Sci. 102, 717–722 (1992)], the disclosure of which is incorporated herein by reference.

To further demonstrate that the entry of the chimeric peptides does not depend of the peptidic sequence linked to pAntp the same experimentation was also performed with other chimeric peptides, encompassing pAntp a peptidic sequence quite different from the sequence of the C-terminal region of Rab3A. However, observation under microscope shows that the internalization and intracellular localization of these chimeric peptide are the same as the ones observed for pAntp and AR3C.

EXAMPLE VII

Coupling of a Peptide or an Oligonucleotide to Helix 3

A peptide having the sequence of the third helix (aa 43–58) of pAntp was synthesized, and a S-S-pyridinium was added in C-ter, using the method described by MATSUEDA et al. [Chemistry Letters, pp 951–952, (1978) and Int. J. of Peptide and Protein Research, pp107–112 (1986)].

For coupling, this peptide was incubated for 2 hours at 37° C. in high salt (1M NaCl) and at neutral pH with an oligonucleotide or oligopeptide bearing a free SH function.

This results in the formation of a fusion product wherein helix 3 and the oligonucleotide or oligopeptide are linked by a disulfide bond.

Alternatively the oligonucleotide or oligopeptide may be provided with an S-S pyridinium, and coupled, in the same way as above, with a peptide comprising the third helix of pAntp and having a free SH function.

EXAMPLE IX

Internalization of an Inhibitor Peptide Linked to Helix 3 of pAntp

An oligopeptide of 12 amino acids length, known as an inhibitor of PKC (protein kinase C) [KEMP et al., Meth. Enzymol., 201 : 287–304 (1991)], was synthesized, and biotinylated on N-terminal NH2. The biotinylated peptide was then linked to the helix 3 peptide as described in example VII above. Either the resulting fusion product, or the inhibitor peptide alone, is added to cultured astrocytes at an extracellular concentration of 10 nM, and incubated with the cells for 2 hours at 37° C.

Internalization of the inhibitor peptide linked to pAntp

The cells were fixed in Ethanol/acetic acid and the biotinylated product visualized under confocal microscopy after labeling with FITC-Streptavidin. Intracellular fluorescence is observed when cells were incubed with the inhibitor peptide linked to the helix 3 peptide, but not when incubation was done with the inhibitor peptide alone.

Inhibition of intracellular PKC $^{32}$P (1 μCi/μl) is added to the culture medium 3 hours before adding the peptide.

After 2 hours incubation with the inhibitor peptide linked to helix 3 peptide, or the inhibitor peptide alone, the cells are lyzed and a phosphorylated protein expressed by astrocytes in culture and bearing 3 Calcium-Calmodulin phosphorylation sites and 2 PKC sites is purified and digested by thermolysin, according to the method decribed by ARAUJOT et al. [J. Biol. Chem., 268, 8, 5911–5920 (1993)]. After bidimensionnal separation, the phosphorylated digestion products are detected by autoradiography.

The same experiment is performed with addition of phorbol, which increases specifically PCK induced phosphorylation.

FIG. 4 (A–D) show the peptidic maps obtained:

Peptides bearing the Calcium-Calmodulin phosphorylation sites are on the right side of the maps. Peptides bearing the PKC phosphorylation sites are on the left side of the maps, and indicated by arrows.

- A. Basal PKC phosphorylation is not antagonized after a 2 hours incubation with the PKC-inhibiting peptide alone.
- B. A 2 hours incubation with the inhibitor peptide linked to the helix 3 peptide completely inhibits phosphorylation of the PKC sites but does not modify phosphorylation of the non-PKC sites.
- C. Incubating the cells with PKC-inhibiting peptide alone does not abolish the increased phosphorylation upon addition of phorbol ester.
- D. Phorbol ester-induced increasement of phosphorylation is abolished by a two hours preincubation with the PKC inhibitor linked to the helix 3 peptide.

EXAMPLE X

Internalization and Biological Effects of Nucleotides Linked to pANTP

Coupling to pAntp:

Oligonucleotides were synthesized with a S-S-Pyridinium in 3', and biotinylated in 5'. For coupling, these oligonucleotides were incubated with pAntp (which comprises a cystine residue localized between helix 2 and 3) as described in Example VII above. This allows a stochiometric coupling between the oligonucleotide and pAntp.

Antisense or sense oligonucleotides corresponding to a 15-mer sequence overlapping the ATG initiation codon of the Amyloid Precursor Protein (APP) gene, were coupled to pAntp as described above, and added to rat cortical neurons in culture. A control experiment was performed with the same oligonucleotides not coupled to pAntp Internalization of the oligonucleotides linked to pAntp After 2 hours the cells were fixed in Ethanol/acetic acid and the biotinylated oligonucleotides were visualized with Streptavidine-Alcalin Phosphatase. Intracellular labeling, which indicates internalization was observed in all cells when they were incubed with the oligonucleotides linked to pAntp. On the other hand, no internalization occurred when cells were incubed with the oligonucleotides alone.

Activity of the internalized oligonucleotides linked to pAntp

After 2 hours incubation with the sense or the antisense oligonucleotide linked to pAntp, the cells were lyzed (2% SDS, 100° C.) and the newly synthesized APP was immunoprecipitated using an anti-APP antibody. Quantification of the immunoprecipitate shows a 50% inhibition in APP biosynthesis after incubation with the antisense oligonucleotide linked to pAntp, compared to the APP biosynthesis after incubation without oligonucleotide or with the sense oligonucleotide linked to pAntp.

As evident from the above, the invention is not in the least limited to its implementations, embodiments and applications which have just been described more explicitly; on the contrary, it embraces all the variants which may come to the mind of a specialist in this field without departing from the framework or the scope of the present invention.

We claim:

1. A macromolecule able to enter a living cell, said macromolecule being selected from the group consisting of:
   (a) a homeobox peptide fragment which comprises helix 3;
   (b) a homeobox peptide bound to a heterologous peptide;
   (c) a homeobox peptide fragment which comprises helix 3 and is bound to a heterologous peptide;
   (d) a homeobox peptide bound to an oligonucleotide; and
   (e) a homeobox peptide fragment which comprises helix 3 and is bound to an oligonucleotide.

2. A macromolecule according to claim 1, wherein said homeobox peptide, or said peptide (a) is bound to a heterologous peptide through a disulfide bridge.

3. A macromolecule able to enter a living cell, said macromolecule being selected from the group consisting of:
   (a') a homeobox peptide fragment which comprises amino acids 43–58 of the homeodomain;
   (b') a homeobox peptide or a homeobox peptide fragment comprising amino acids 43–58 of the homeodomain, wherein said homeobox peptide or homeobox peptide fragment has an Ala residue in position 50 of the homeodomain, and a Tyr residue in position 36 of the homeodomain;
   (c') a homeobox peptide or a homeobox peptide fragment comprising amino acids 43–58 of the homeodomain, wherein said homeobox peptide or homeobox peptide fragment has a Pro residue in position 40 of the homeodomain, and a Pro residue in position 41 of the homeodomain;
   (d') said peptide (a'), (b') or (c') bound to an oligonucleotide; and
   (e') said peptide (a'), (b') or (c') bound to a heterologous peptide.

4. The macromolecule according to claim 3, wherein said peptide (a'), (b'), or (c') in (d') is bound to said oligonucleotide through a disulfide bridge.

5. The macromolecule according to claim 3, wherein said peptide (a'), (b'), or (c') in (e') is bound to said heterologous peptide through a disulfide bridge.

6. A method for introducing a macromolecule into a living cell, which comprises contacting said living cell with said macromolecule, which is a derivative of a homeobox peptide selected from the group consisting of:
   (a') a fragment of a homeobox peptide comprising amino acids 43–58 of the homeodomain;
   (b') a homeobox peptide or a fragment thereof comprising amino acids 43–58 of the homeodomain wherein said homeobox peptide or fragment thereof has an Ala residue in position 50 of the homeodomain, and a Tyr residue in position 36 of the homeodomain;
   (c') a homeobox peptide or a fragment thereof comprising amino acids 43–58 of the homeodomain wherein said homeobox peptide or fragment thereof has a Pro residue in position 40 of the homeodomain, and a Pro residue in position 41 of the homeodomain;
   (d') said peptide (a'), (b') or (c') bound to an oligonucleotide;
   (e') said peptide (a'), (b') or (c') bound to a heterologous peptide.

7. The method according to claim 6, wherein said homeobox peptide, said fragment of the homeobox peptide comprising helix 3, or peptide (a'), (b'), or (c') is bound to a heterologous peptide through a disulfide bridge.

8. The method according to claim 6, wherein said homeobox peptide, or fragment of a homeobox peptide comprising helix 3 or said peptide (a'), (b'), or (c') is bound to an oligonucleotide through a disulfide bridge.

9. The method according to claim 6, wherein said living cell contacted with said macromolecule is at least one of the cells of a cell culture.

10. A cultured cell treated by the method of claim 9.

11. The method according to claim 6, wherein said living cell is a neuron.

12. The method according to claim 6, wherein said peptide (a'), (b'), or (c') is produced recombinantly.

13. A method for introducing a macromolecule into a living cell, which method comprises contacting said living cell with said macromolecule, which is a homeobox pevtide or a derivative thereof selected from the group consisting of:
   (a) a fragment of a homeobox peptide comprising helix 3;
   (b) a homeobox peptide, or said peptide (a) bound to a heterologous peptide; and
   (c) a fragment of a homeobox peptide comprising helix 3 bound to an oligonucleotide.

14. The method according to claim 13, wherein the macromolecule transported into the living cell is a homeobox peptide, which is active as a cellular growth factor.

15. A cultured cell treated by the method of claim 14.

16. The method according to claim 13, wherein the living cell contacted with said macromolecule is at least one of the cells of a cell culture.

17. The method according to claim 13, wherein the living cell is a neuron.

18. The method according to any one of claims 13 or 14 to 17 wherein the homeobox peptide is the peptide pAntp.

19. The method according to claim 13, wherein said homeobox peptide or said fragment of a homeobox peptide is produced recombinantly.

20. A method according to claim 13, wherein said homeobox peptide, or said fragment of a homeobox peptide is bound to a heterologous peptide through a disulfide bridge.

* * * * *

UNITED STATES PATENT AND TRADEMARK OFFICE
CERTIFICATE OF CORRECTION

PATENT NO. : 5,888,762

DATED : March 30, 1999

INVENTOR(S): Alain JOLIOT et al.

It is certified that an error appears in the above-identified patent and that said Letters Patent is hereby corrected as shown below:

On the title page, item [30], the Foreign Application Priority Data should read:

--Jun. 5, 1990 [FR] France .................................90/06912--

Signed and Sealed this

Twenty-fourth Day of August, 1999

Attest:

Q. TODD DICKINSON

*Attesting Officer*    *Acting Commissioner of Patents and Trademarks*